US010438699B2

(12) United States Patent
Liang et al.

(10) Patent No.: US 10,438,699 B2
(45) Date of Patent: Oct. 8, 2019

(54) METHOD AND SYSTEM FOR DETERMINING AN ASSOCIATION OF BIOLOGICAL FEATURES WITH A MEDICAL CONDITION

(71) Applicant: Macau University of Science and Technology, Taipa (MO)

(72) Inventors: Yong Liang, Taipa (MO); Hai-Hui Huang, Taipa (MO); Xiao-Ying Liu, Taipa (MO)

(73) Assignee: MACAU UNIVERSITY OF SCIENCE AND TECHNOLOGY, Taipa (MC)

( * ) Notice: Subject to any disclaimer, the term of this patent is extended or adjusted under 35 U.S.C. 154(b) by 646 days.

(21) Appl. No.: 15/150,608

(22) Filed: May 10, 2016

(65) Prior Publication Data

US 2017/0329912 A1    Nov. 16, 2017

(51) Int. Cl.
*G06N 7/02* (2006.01)
*G16H 50/20* (2018.01)
*G06N 5/02* (2006.01)

(52) U.S. Cl.
CPC .............. *G16H 50/20* (2018.01); *G06N 5/02* (2013.01); *G06N 7/023* (2013.01)

(58) Field of Classification Search
None
See application file for complete search history.

(56) References Cited

U.S. PATENT DOCUMENTS

| 2016/0163574 | A1* | 6/2016 | Chang | G06N 7/00 702/81 |
| 2018/0327848 | A1* | 11/2018 | Ayers | C07K 16/2818 |
| 2018/0374210 | A1* | 12/2018 | Barker | G06T 7/0012 |

OTHER PUBLICATIONS

"Sparse logistic regression with a L1/2 penalty for gene selection in cancer classification," Yong Liang, Cheng Liu, Xin-Ze Luan, Kwong-Sak Leung, Tak-Ming Chan, Zong-Ben Xu, and Hai Zhang, BMC Bioinformatics 2013, 14:198 (Year: 2013).*
"L1/2 regularization," Xu ZongBen, Zhang Hai, Wang Yao, Chang XiangYu & Liang Yong, Science China, Jun. 2010 vol. 53 No. 6: 1159-1169 (Year: 2010).*
"Sparse kernel logistic regression based on L1/2 regularization," Xu Chen, Peng ZhiMing & Jing WenFeng, Science China, Apr. 2013, vol. 56 042308:1-042308:16 (Year: 2013).*
"Honest variable selection in linear and logistic regression models via $\ell 1$ and $\ell 1 + \ell 2$ penalization," Florentina Buena, Electronic Journal of Statistics, vol. 2 (2008) 1153-1194 ISSN: 1935-7524, DOI: 10.1214/08-EJS287 (Year: 2008).*

(Continued)

*Primary Examiner* — Hal Schnee
(74) *Attorney, Agent, or Firm* — Renner Kenner Greive Bobak Taylor & Weber (57) ABSTRACT

A system and a method for determining an association of one or more biological features with a medical condition provides empirical results and simulations confirming that the involvement of both $L_{1/2}$-regularized logistic regression and $L_2$-regularized logistic regression in the regression model is highly competitive against usual approaches like Lasso, $L_{1/2}$, SCAD-$L_2$, and Elastic net in analyzing high dimensional and low sample sizes data.

13 Claims, 5 Drawing Sheets

(56) References Cited

OTHER PUBLICATIONS

"Application of L1/2 regularization logistic method in heart disease diagnosis," Bowen Zhang, Hua Chai, Ziyi Yang, Yong Liang, Gejin Chu and Xiaoying Liu, Bio-Medical Materials and Engineering 24 (2014) 3447-3454, DOI 10.3233/BME-141169 (Year: 2014).*
R. Tibshirani, "Regression Shrinkage and Selection via the Lasso", J. R. Statist. Soc. B, JSTOR; vol. 58, No. 1 (1996), pp. 267-288.
J. Fan et al. (2001): "Variable Selection via Nonconcave Penalized Likelihood and its Oracle Properties", Journal of American Statistical Association, 96:456, pp. 1348-1360.
H. Zou (2006): "The Adaptive Lasso and its Oracle Properties", Journal of American Statistical Association, 101:476, pp. 1418-1429.
N. Meinshausen et al., "Lasso-Type Recovery of Sparse Representations for High-Dimensional Data", The Annals of Statistics, JSTOR; vol. 37, No. 1 (Feb. 2009), pp. 246-270.
Z. Xu et al., "L1/2 Regularization", Science China Information Sciences, Springer; 2010; vol. 53, No. 6; pp. 1159-1169.
J. Zeng et al., "L1/2 Regularization: Convergence of Iterative Half Thresholding Algorithm", IEEE Transactions on Signal Processing, vol. 62,. No. 9, May 2014, pp. 2317-2329.
Z. Xu et al., "L1/2 Regularization: A Thresholding Representation Theory and a Fast Solver", IEEE Transactions on Neural Networks and Learning Systems, vol. 23, No. 7, Jul. 2012, pp. 1013-1027.
M.R. Segal et al., "Regression Approaches for Microarray Data Analysis", Journal of Computational Biology, Mary Ann Liebert, Inc., vol. 10, Nov. 6, 2003, pp. 961-980.
H. Zou et al., "Regularization and Variable Selection via the Elastic Net", J. R. Statist. Soc. B, Wiley Online Library, 2005, 67, pp. 301-320.
N. Becker et al., "Elastic SCAD as a Novel Penalization Method for SVM Classification Tasks in High-Dimensional Data", BMC Bioinformatics, 2011, 12:138, pp. 1-13.
L. Zeng et al. (2014) "Group Variable Selection via SCAD-L2 ", Statistics: A Journal of Theoretical and Applied Statistics, 48:1, pp. 49-66.
P. Zhao et al., "Stagewise Lasso", Journal of Machine Learning Research JMLR. org., 2007, 8: pp. 2701-2726.
E. Candes et al., "The Dantzig Selector: Statistical Estimation when p is Much Larger than n1", The Annals of Statistics, JSTOR; vol. 35, No. 6 (2007), pp. 2313-2351.
K. Knight et al., "Asymptotics for Lasso-Type Estimators", The Annals of Statistics, JSTOR; vol. 28, No. 5 (Oct. 2000), pp. 1356-1378.
D. Malioutov et al., "A Sparse Signal Reconstruction Perspective for Source Localization with Sensor Arrays", IEEE Transactions on Signal Processing, vol. 53, No. 8, Aug. 2005, pp. 3010-3022.
Y. Liang et al., "Sparse Logistic Regression with a L1/2 Penalty for Gene Selection in Cancer Classification", BMC Bioinformatics, 2013, 14:198, pp. 1-12.
H-H Huang et al., "Network-Based Logistic Classification with an Enhanced L1/2 Solver Reveals Biomarker and Subnetwork Signatures for Diagnosing Lung Cancer", BioMed Research International, Hindawi Publishing Corporation, vol. 2015, Article ID 713953, pp. 1-7.
J. H. Friedman, "Regularized Discriminant Analysis", Journal of American Statistical Association, Taylor & Francis, 1989, 84: pp. 165-175 (original source document provided herewith consists of pp. 1-32).
T. Hastie et al., "The Elements of Statistical Learning: Data Mining, Inference and Prediction", Math Intell., Springer, 2005, vol. 27, No. 2, pp. 83-85.
J. Friedman et al., "Regularization Paths for Generalized Linear Models via Coordinate Descent", Journal fo Statistical Software, NIH Public Access, Jan. 2010, vol. 33, No. 1, pp. 1-22.
P. Breheny et al., "Coordinate Descent Algorithmns for Nonconvex Penalized Regression, with Applications to Biological Feature Selection", Annals of Applied Statistics. NIH Public Access; 2011, vol. 5, No. 1, 232-253.
W. Zhang et al., "Molecular Pathway Identification Using Biological Network-Regularized Logistic Models", BMC Genomics, England, 2013, 14 (Suppl. 8):57; Epub Dec. 9, 2013. doi: 10.1186/1471-2164-14-S8-S7 [doi], pp. 1-8.
D. Singh et al., "Gene Expression Correlates of Clinical Prostate Cancer Behavior", Cancer Cell: Mar. 2002, vol. 1, pp. 203-209.
E. Glaab et al., "Using Rule-Based Machine Learning for Candidate Disease Gene Prioritization and Sample Classification of Cancer Gene Expression Data", PLoS One, Public Library of Science, Jul. 2012, vol. 7, Issue 7, e39932, pp. 1-18.
M.A. Shipp et al., "Diffuse Large B-Cell Lymphoma Outcome Prediction by Gene-Expression Profiling and Supervised Machine Learning", Nature Medicine, Nature Publishing Group, Jan. 2002, vol. 8, No. 1, pp. 68-74.
J-S Seo et al., "The Transcriptional Landscape and Mutational Profile of Lung Adenocarcinoma", Genome Research, Genome Medicine Institute (GMI), 2012, 22, 2109-2119.
B. Bartling et al., "Down-Regulation of the Receptor for Advanced Glycation End-Products (RAGE) Supports Non-Small Cell Lung Carcinoma", Carcinogenesis, 2005, vol. 26, No. 2, pp. 293-301.
S.T. Buckley et al., "The Receptor for Advanced Glycation End Products (RAGE) and the Lung", Journal of Biomedicine and Biotechnology, vol. 2010, Article ID 917108, pp. 1-11.
R. Jing et al., "Receptor for Advanced Glycation End Products (RAGE) Soluble Form (sRAGE): a new biomarker for lung cancer", Neoplasma, 57, 1, 2010, pp. 55-61.
T. Kelkka et al., "Mice Lacking NCF1 Exhibit Reduced Growth of Implanted Melanoma and Carcinoma Tumors", PLos One, Public Library of Science, Dec. 2013, vol. 8, No. 12, e84148, pp. 1-10.
H. Vuong et al., "Functional Consequences of Somatic Mutations in Cancer Using Protein Pocket-Based Prioritization Approach", Genome Medicine 2014, 6:81, pp. 1-14.
C. Ambroise et al., "Selection Bias in Gene Extraction on the Basis of Microarray Gene-Expression Data", PNAS, May 14, 2002, vol. 99, No. 10, pp. 6562-6566.
T.K. Paul et al., "Extraction of Informative Genes from Microarray Data", Proceedings of the 7th Annual Conference on Genetic and Evolutionary Computation. ACM, 2005, pp. 453-460.
L. F. A. Wessels et al., "A Protocol for Building and Evaluating Predictors of Disease State Based on Microarray Data", Bioinformatics, 2005, vol. 21, No. 19, pp. 3755-3762.
L. Shen et al., "Dimension Reduction-Based Penalized Logistic Regression for Cancer Classification Using Microarray Data", IEEE/ACM Transactions on Computational Biology and Bioinformatics, Apr.-Jun. 2005, vol. 2, No. 2, pp. 166-175.
M. Lecocke et al., "An Empirical Study of Univariate and Genetic Algorithm-Based Feature Selection in Binary Classification with Microarray Data", Cancer Informatics, 2006, 2, pp. 313-327.
O. Dagliyan et al., "Optimization Based Tumor Classification from Microarray Gene Expression Data", PLos One, Public Library of Science, Feb. 2011, vol. 6, No. 2, e14579, pp. 1-10.
J. Liu et al., "Tumor Classification Based on Gene Microarray Data and Hybrid Learning Method", Machine Learning and Cybernetics, 2003 International Conference. IEEE, 2003. pp. 2275-2280.
L. Goh et al., "A Novel Feature Selection Method to Improve Classification of Gene Expression Data", Australian Computer Society, Inc., 2004. pp. 161-166.
Y. Hu et al., "Ontology-Based Framework for Personalized Diagnosis and Prognosis of Cancer Based on Gene Expression Data", Neural Information Processing, Springer, 2008, pp. 846-855.

* cited by examiner

METHOD AND SYSTEM FOR DETERMINING AN ASSOCIATION OF BIOLOGICAL FEATURES WITH A MEDICAL CONDITION

TECHNICAL FIELD

The present invention relates to a system and a method for determining an association of one or more biological features with a medical condition, in particularly, but not exclusively, to a system for determining an association of one or more of presence of genes, gene expression, presence of gene products or amount of gene products with cancer, in particular for determining an association of the expression of one or more genes with cancer or a specific cancer subtype.

BACKGROUND

Cancer classification and feature (gene) selection plays an important role in knowledge discovery in genomic data.

With advances in high-throughput molecular techniques, researchers can study the expression of tens thousands of genes simultaneously. Cancer classification based on gene expression levels is one of the central problems in genome research. Logistic regression is a popular classification method and has an explicit statistical interpretation which can obtain probabilities of classification regarding the cancer phenotype. However, in most gene expression studies, the number of genes typically far exceeds the number of sample sizes. This situation is called high dimensional and low sample size problem and the normal logistic regression method cannot be directly used to obtain the parameter estimates. Thus, although logistic regression is one of the most popular classification methods, it does unfortunately not achieve the purpose of the feature selection.

There remains a strong need for methods and related systems sufficiently dealing with the problem of highly correlated variables and the high dimensional and low sample size problem, i.e. those which are suitable for feature selection in particular in the medical field. Clearly, having a fast and reliable analysis of features could significantly contribute to an improved diagnosis of diseases and treatment selection.

SUMMARY OF THE INVENTION

In accordance with a first aspect of the present invention, there is provided a method for determining an association of one or more biological features with a medical condition, comprising the steps of:

obtaining a dataset comprising biological data related to a plurality of samples each having a plurality of biological features;

applying at least some of the biological data to a regression model to determine and/or optimize parameters in the regression model thereby solving the regression model; and processing the biological data using the solved regression model to determine one or more biological features that are associated with the medical condition;

wherein the regression model involves the use of both $L_{1/2}$-regularized logistic regression and $L_2$-regularized logistic regression.

The expression "association of one or more biological features with a medical condition" generally means any kind of expected link or connection between both, in an embodiment "association" means that the medical condition is or is expected to be a) caused by the one or more biological features, b) the one or more biological features at least contribute to the medical condition or its clinical worsening, and/or c) the one or more biological features are involved in cellular processes which cause or contribute or are expected to cause or contribute to the medical condition or its clinical worsening.

In an embodiment, the regression model involves the use of a linear combination of $L_{1/2}$-regularized logistic regression and $L_2$-regularized logistic regression.

In an embodiment, the dataset is represented as:

$$D=\{(X_1,y_1),(X_2,y_2),\ldots,(X_n,y_n)\},$$

where n is a number of the plurality of samples, p is a number of the plurality of biological features, $X_i=(x_{i1}, x_{i2}, \ldots, x_{ip})$ is the $i^{th}$ sample with p biological features, and $y_i$ is a corresponding dependent variable. The regression model is in an embodiment, in particular in the aforementioned embodiment, defined at least partly by:

$$L(\lambda, \alpha, \beta) = -\sum_{i=1}^{n}\{y_i\log[f(X_i'\beta)] + (1-y_i)\log[1-f(X_i'\beta)]\} + \lambda\left(\alpha|\beta|^{\frac{1}{2}} + (1-\alpha)|\beta|^2\right)$$

where $\beta=(\beta_1, \ldots, \beta_p)$ are the coefficients to be determined and/or optimized, and $\lambda$ and $\alpha$ are predetermined values. In the afore-mentioned embodiment, in particular $\lambda=1$ and $\alpha=0.2$.

In an embodiment, such as in an afore-mentioned embodiment, the parameters in the regression model are determined and/or optimized using a coordinate descent optimization method. Said coordinate descent optimization method in a further embodiment comprises the steps of:

optimizing the regression model using at least some of the biological data, by varying one of the parameters in the regression model while fixing the other parameters in the regression model;

updating the parameters in the regression model; and repeating the optimization and update steps for at least once for each of the parameters in the regression model so as to optimize the regression model.

The repeating step continues in an embodiment until a convergence condition relating to the parameters in the regression model is reached.

In an embodiment, the method of the present invention further comprises the step of ranking the biological features determined to be associated with the medical condition according to their degree of association with the medical condition.

In an embodiment, the plurality of samples according to the method of the present invention is taken from animals or humans, at least some of which have the medical condition. In a further embodiment, the plurality of samples is taken from mammals and in particular from humans, at least some of which have the medical condition.

In an embodiment, the samples are of human tissue like cancerous tissue.

In an embodiment, the medical condition includes and in particular is cancer.

In an embodiment, the plurality of biological features is one or more of: presence of a gene, gene expression, presence of a gene product or amount of a gene product. In a particular embodiment, the at least one gene represents a biomarker such as for cancer or a specific cancer subtype.

In accordance with a second aspect of the present invention, there is provided a system for determining an association of one or more biological features with a medical condition, comprising:

one or more processors arranged to apply at least some biological data in a dataset comprising biological data related to a plurality of samples each having a plurality of biological features to a regression model so as to determine and/or optimize parameters in the regression model thereby solving the regression model; and process the biological data using the solved regression model so as to determine one or more biological features that are associated with the medical condition;

wherein the regression model involves the use of both $L_{1/2}$-regularized logistic regression and $L_2$-regularized logistic regression.

In an embodiment of the system of the present invention, the regression model involves the use of a linear combination of $L_{1/2}$-regularized logistic regression and $L_2$-regularized logistic regression.

In an embodiment of the system of the present invention, the dataset is represented as:

$$D=\{(X_1,y_1),(X_2,y_2),\ldots,(X_n,y_n)\},$$

where n is a number of the plurality of samples, p is a number of the plurality of biological features, $X_i=(x_{i1}, x_{i2}, \ldots, x_{ip})$ is the $i^{th}$ sample with p biological features, and $y_i$ is a corresponding dependent variable. The regression model is in an embodiment of the system of the present invention, in particular in the afore-mentioned embodiment, defined at least partly by:

$$L(\lambda, \alpha, \beta) = -\sum_{i=1}^{n}\{y_i\log[f(X_i'\beta)] + (1-y_i)\log[1-f(X_i'\beta)]\} + \lambda\left(\alpha|\beta|^{\frac{1}{2}} + (1-\alpha)|\beta|^2\right)$$

where $\beta=(\beta_1,\ldots,\beta_p)$ are the coefficients to be optimized, and $\lambda$ and $\alpha$ are predetermined values. In the afore-mentioned embodiment, in particular $\lambda=1$ and $\alpha=0.2$.

In an embodiment of the system of the present invention, the one or more processors are further arranged to determine and/or optimize the parameters in the regression model by optimizing the regression model using at least some of the data, through varying one of the parameters in the regression model while fixing the other parameters in the regression model;

updating the parameters in the regression model; and repeating the optimization and update steps for at least once for each of the parameters in the regression model until a convergence condition relating to the parameters in the regression model is reached.

In an embodiment of the system of the present invention, the one or more processors are further arranged to rank the biological features determined to be associated with the medical condition according to their degree of association with the medical condition.

In an embodiment of the system of the present invention, the plurality of samples is taken from animals or humans, at least some of which have the medical condition. In further embodiments, the plurality of samples is taken from mammals and in particular from humans, at least some of which have the medical condition.

In an embodiment of the system of the present invention, the samples are of human tissue like cancerous tissue.

In an embodiment of the system of the present invention, the medical condition includes and in a particular embodiment is cancer.

In an embodiment of the system of the present invention, the plurality of biological features is one or more of: presence of a gene, gene expression, presence of a gene product or amount of a gene product. In a particular embodiment, the at least one gene represents a biomarker such as for cancer or a specific cancer subtype.

In an embodiment, the system of the present invention further comprises a display arranged to display the determination result.

In accordance with a third aspect of the present invention, there is provided a non-transient computer readable medium for storing computer instructions that, when executed by one or more processors, causes the one or more processors to perform a method for determining an association of one or more biological features with a medical condition, comprising the steps of:

applying at least some biological data in a dataset comprising biological data related to a plurality of samples each having a plurality of biological features to a regression model so as to determine and/or optimize parameters in the regression model thereby solving the regression model; and processing the biological data using the solved regression model so as to determine one or more biological features that are associated with the medical condition;

wherein the regression model involves the use of both $L_{1/2}$-regularized logistic regression and $L_2$-regularized logistic regression.

In an embodiment of the non-transient computer readable medium of the present invention, the regression model involves the use of a linear combination of $L_{1/2}$-regularized logistic regression and $L_2$-regularized logistic regression.

In an embodiment of the non-transient computer readable medium of the present invention, the dataset is represented as:

$$D=\{(X_1,y_1),(X_2,y_2),\ldots,(X_n,y_n)\},$$

where n is a number of the plurality of samples, p is a number of the plurality of biological features, $X_i=(x_{i1}, x_{i2}, \ldots, x_{ip})$ is the $i^{th}$ sample with p biological features, and $y_i$ is a corresponding dependent variable. In an embodiment, in particular in the afore-mentioned embodiment, the regression model is defined at least partly by:

$$L(\lambda, \alpha, \beta) = -\sum_{i=1}^{n}\{y_i\log[f(X_i'\beta)] + (1-y_i)\log[1-f(X_i'\beta)]\} + \lambda\left(\alpha|\beta|^{\frac{1}{2}} + (1-\alpha)|\beta|^2\right)$$

where $\beta=(\beta_1,\ldots,\beta_p)$ are the coefficients to be optimized, and $\lambda$ and $\alpha$ are predetermined values. In the afore-mentioned embodiment, in particular $\lambda=1$ and $\alpha=0.2$.

In an embodiment of the non-transient computer readable medium of the present invention, the one or more processors are further arranged to determine and/or optimize the parameters in the regression model by optimizing the regression model using at least some of the data, through varying one of the parameters in the regression model while fixing the other parameters in the regression model;

updating the parameters in the regression model; and repeating the optimization and update steps for at least once for each of the parameters in the regression model until a convergence condition relating to the parameters in the regression model is reached.

In an embodiment, the one or more processors can be further arranged to rank the biological features determined to be associated with the medical condition according to their degree of association with the medical condition.

In an embodiment of the non-transient computer readable medium of the present invention, the plurality of samples are taken from animals or humans. In further embodiments, the plurality of samples is taken from mammals and in particular from humans at least some of which have the medical condition.

In an embodiment, the samples are of human tissue like cancerous tissue.

The medical condition in an embodiment includes and in a further embodiment is cancer.

The plurality of biological features is in an embodiment of the non-transient computer readable medium one or more of: presence of a gene, gene expression, presence of a gene product or amount of a gene product. In a particular embodiment, the at least one gene represents a biomarker such as for cancer or a specific cancer subtype.

Other features and aspects of the invention will become apparent by consideration of the following detailed description and accompanying drawings.

BRIEF DESCRIPTION OF THE DRAWINGS

FIG. 3A shows exact solutions of Lasso, FIG. 3B of $L_{1/2}$, FIG. 3C of Elastic net, and FIG. 3D of HLX in an orthogonal design.

DETAILED DESCRIPTION OF THE INVENTION

The inventors based on their research, tests and experiments concluded that a regularization method can be used in order to deal with the problem of high dimensionality. A well-known regularization method is the $L_1$ penalty (Tibshirani R., J R Stat Soc B. JSTOR; 1996; 267-288), which is the least absolute shrinkage and selection operator (Lasso). It is performing continuous shrinkage and gene selection at the same time. Other $L_1$ norm type regularization methods include the smoothly-clipped-absolute-deviation (SCAD) penalty (Fan J., Li R., J Am Stat Assoc. Taylor & Francis; 2001; 96: 1348-1360) which is symmetric, nonconcave, and has singularities at the origin to produce sparse solutions. The adaptive Lasso (Zou H., J Am Stat Assoc. Taylor & Francis; 2006; 101: 1418-1429) where adaptive weights are employed to penalize different coefficients in the $L_1$ penalty. However, the $L_1$ type regularization may yield inconsistent feature selections in some situations (Zou H., J Am Stat Assoc; 2006; 101: 1418-1429) and often introduces extra bias in estimation (Meinshausen N., Yu B., Ann Stat. JSTOR; 2009; 246-270).

Xu et al. (Xu Z. et al., Sci China Inf Sci. Springer; 2010; 53: 1159-1169) proposed the $L_{1/2}$ penalty, a method that can be taken as a representative of $L_q$ ($0<q<1$) penalties in both sparsity and computational efficiency, and has demonstrate many attractive properties, such as unbiasedness, and oracle properties (Xu Z. et al., Sci China Inf Sci. Springer; 2010; 53: 1159-1169, Zeng J. et al., Signal Process IEEE Trans. IEEE; 2014; 62: 2317-2329, Xu Z. et al., IEEE Trans neural networks Learn Syst. United States; 2012; 23: 1013-1027, doi:10.1109/TNNLS.2012.2197412 [doi]). However, similar to most of regularization methods, the $L_{1/2}$ penalty ignores the correlation between features, and is consequently unable to analyze data with dependent structures. If there is a group of variables among which the pair-wise correlations are very high, then the $L_{1/2}$ method tends to select only one variable that represents the corresponding group.

In gene expression study, genes are often highly correlated if they share the same biological pathway (Segal M R. et al, J Comput Biol. Mary Ann Liebert, Inc.; 2003; 10: 961-980). Some efforts had been made to deal with the problem of highly correlated variables. Zhou and Hastie proposed Elastic net penalty (Zou H, Hastie T., J R Stat Soc Ser B., Wiley Online Library; 2005; 67: 301-320) which is a linear combination of $L_1$ and $L_2$ (the ridge technique) penalties, and such method emphasizes a grouping effect, where strongly correlated genes tend to be in or out of the model together. Becker et al. (Becker N. et al., BMC Bioinformatics. German Cancer Research Center, Division Molecular Genetics, INF 280, 69120 Heidelberg; 2011; 12: 138. doi:10.1186/1471-2105-12-138 [doi]) proposed the Elastic SCAD (SCAD-$L_2$), a combination of SCAD and $L_2$ penalties. By introducing the $L_2$ penalty term, Elastic SCAD also works for the groups of predictors.

Without being bound by theory, the inventors herein through their research, tests and experiments discovered that a HLX approach with involvement of both, $L_{1/2}$-regularized logistic regression and $L_2$-regularized logistic regression in the regression model, can be advantageously applied when determining an association of biological features with a medical condition.

In this embodiment, the system for determining an association of biological features with a medical condition is implemented by or for operation on a computer having an appropriate user interface. The computer may be implemented by any computing architecture, including stand-alone PC, client/server architecture, "dumb" terminal/mainframe architecture, or any other appropriate architecture. The computing device is appropriately programmed to implement the invention.

Figure 1:
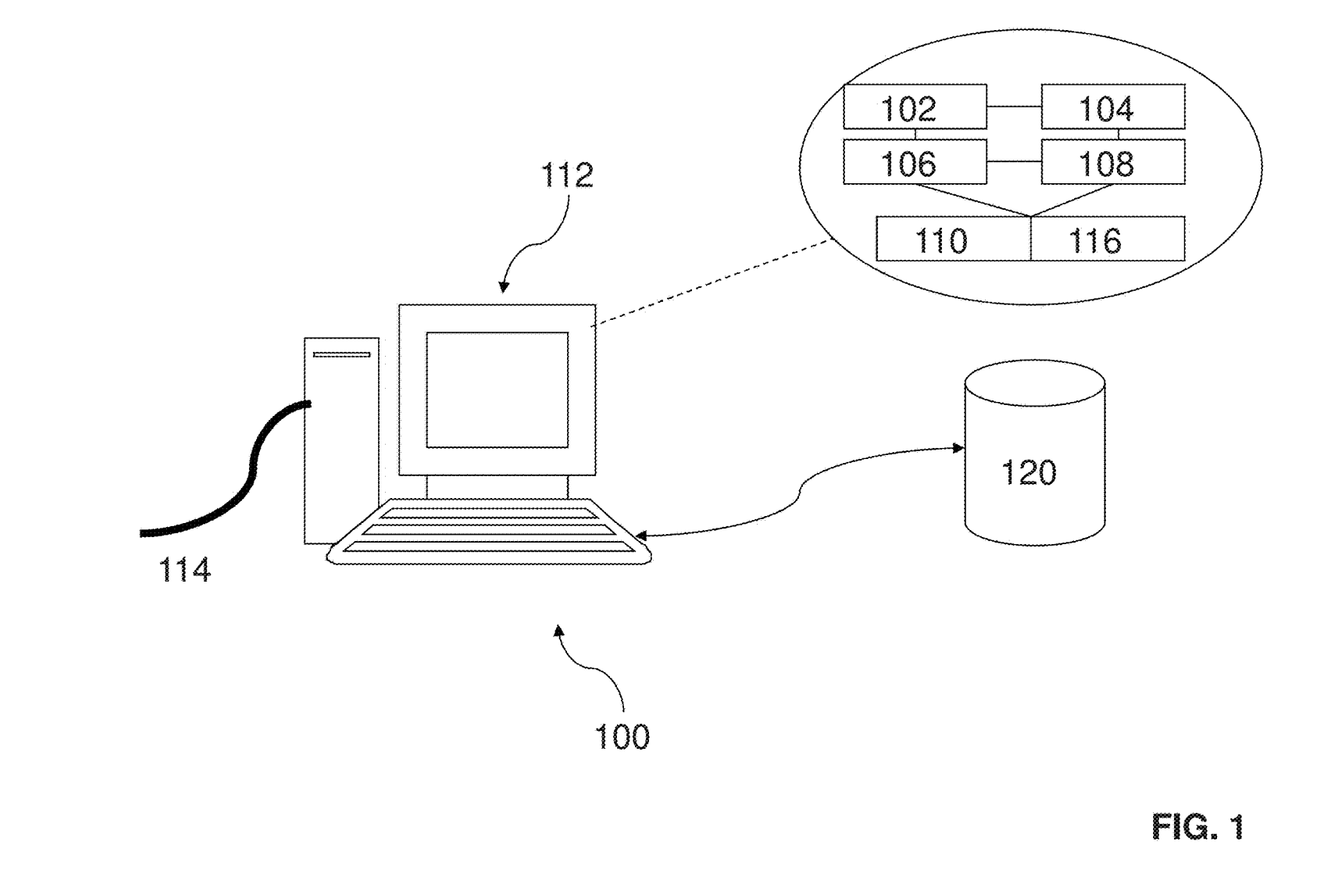
FIG. 1 is a schematic diagram of a computer or computing server arranged to operate a system of the present invention for determining an association of one or more biological features with a medical condition.

Referring to FIG. 1, there is a shown a schematic diagram of a computer or a computing server 100 which in this embodiment comprises a server 100 arranged to operate, at least in part if not entirely, the system for determining an association of one or more biological features with a medical condition in accordance with one embodiment of the present invention. The server 100 comprises suitable components necessary to receive, store and execute appropriate computer instructions. The components may include a processing unit 102, read-only memory (ROM) 104, random access memory (RAM) 106, and input/output devices such as disk drives 108, input devices 110 such as an Ethernet port, a USB port, etc., display 112 such as a liquid crystal display, a light emitting display or any other suitable display and communications links 114. The server 100 includes instructions that may be included in ROM 104, RAM 106 or disk drives 108 and may be executed by the processing unit 102. There may be provided a plurality of communication links 114 which may variously connect to one or more computing devices such as a server, personal computers, terminals, wireless or handheld computing devices. At least one of a plurality of communications link may be connected to an external computing network through a telephone line or other type of communications link.

The server 100 may include storage devices such as a disk drive 108 which may encompass solid state drives, hard disk drives, optical drives or magnetic tape drives. The server 100 may use a single disk drive or multiple disk drives. The server 100 may also have a suitable operating system 116 which resides on the disk drive or in the ROM of the server 100.

The system has a database 120 residing on a disk or other storage device which is arranged to store a dataset. The database 120 is in communication with the server 100 with an interface, which is implemented by computer software residing on the server 100. Alternatively, the database 120 may also be implemented as a stand-alone database system in communication with the server 100 via an external computing network, or other types of communication links.

Figure 2:
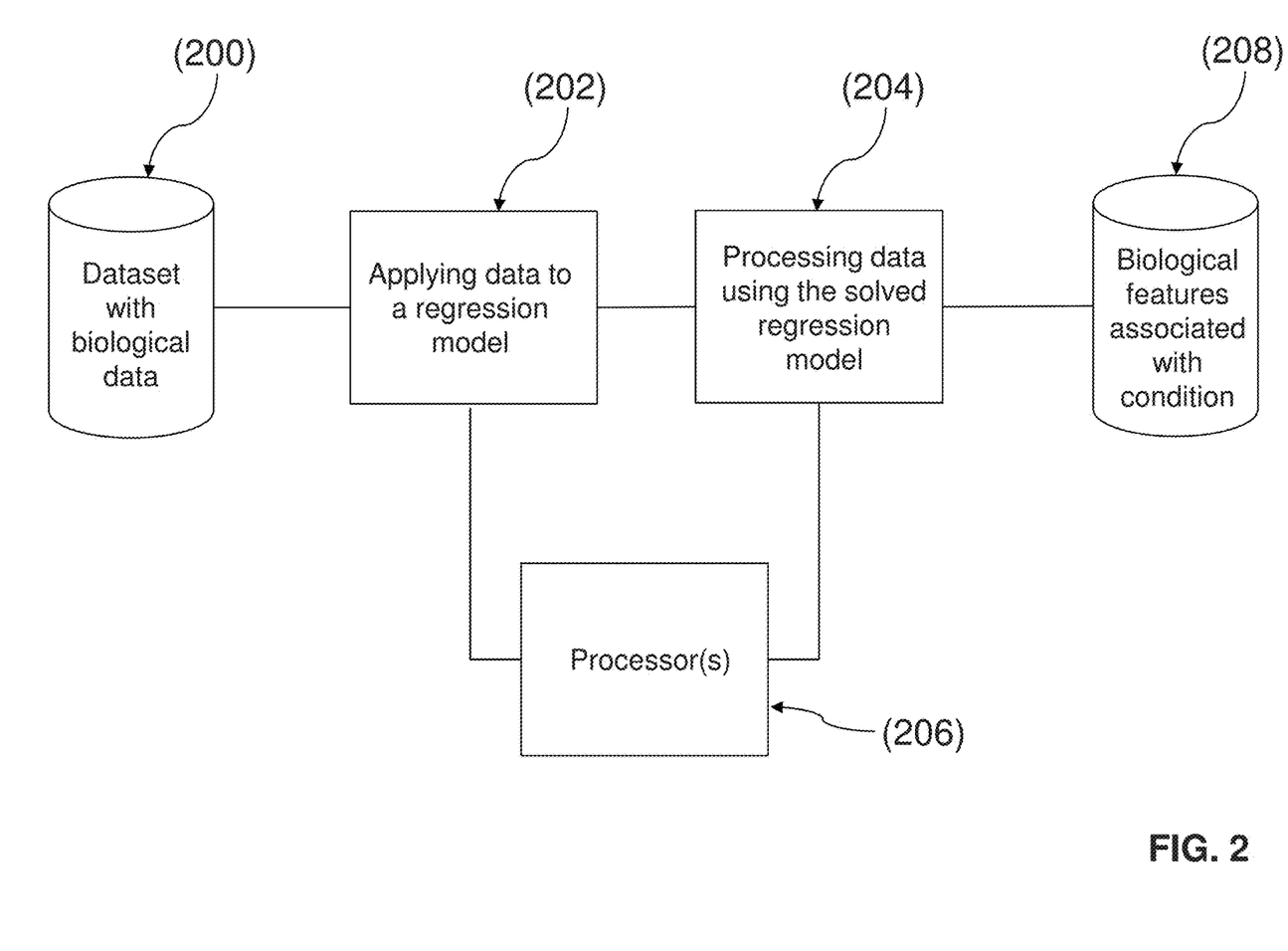
FIG. 2 is a schematic diagram showing a system of the present invention for determining an association of one or more biological features with a medical condition.
Figure 3A:
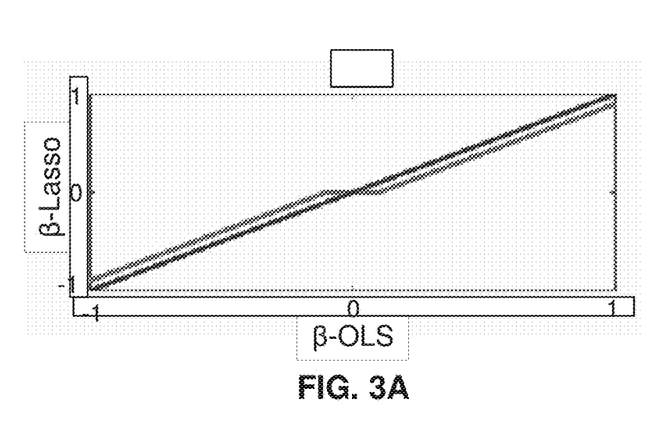
FIGS. 3A, 3B, 3C, and 3D show exact solutions of Lasso, $L_{1/2}$, Elastic net, and HLX in an orthogonal design. The regularization parameters are $\lambda=0.1$ and $\alpha=0.8$ for Elastic net and HLX ($\beta$-OLS is the ordinary least-squares (OLS) estimator).
Figure 3B:
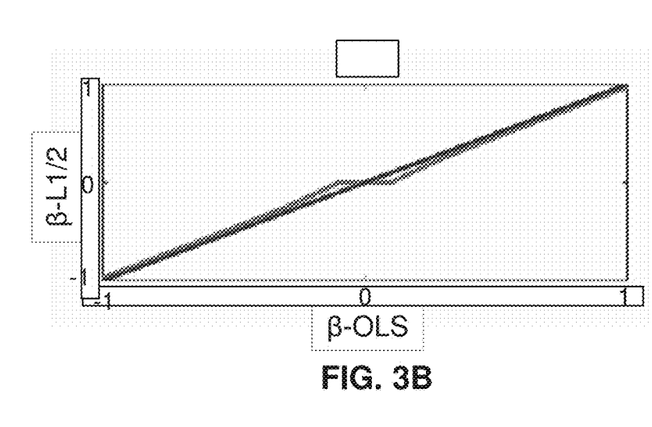
Figure 3C:
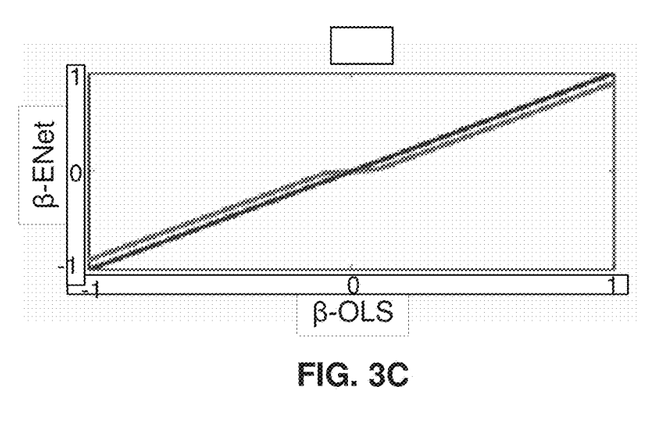
Figure 3D:
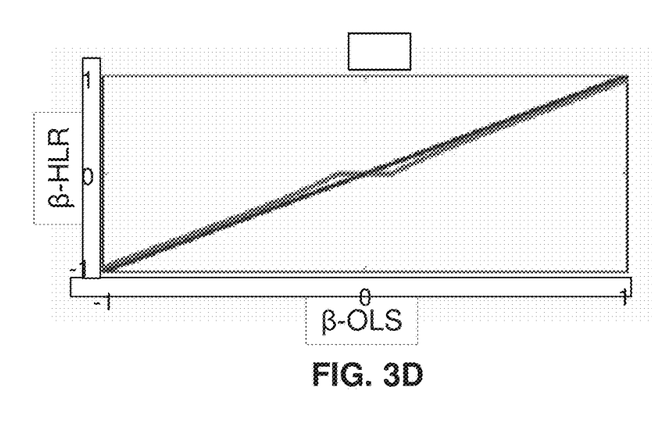

With reference to FIG. 2, there is provided a system for determining an association of biological features with a medical condition, comprising:

one or more processors 206 arranged to apply at least some biological data in a dataset (200) comprising biological data related to a plurality of samples each having a plurality of biological features to a regression model (202) so as to determine and/or optimize parameters in the regression model thereby solving the regression model; and process the biological data using the solved regression model (204) so as to determine one or more biological features (208) that are associated with the medical condition;

wherein the regression model involves the use of both $L_{1/2}$-regularized logistic regression and $L_2$-regularized logistic regression.

In this embodiment, the system may include one or more processors (206) each arranged to apply at least some biological data in a dataset (200) comprising biological data related to a plurality of samples from cancerous tissue from humans each having a plurality of biological features, namely presence of a gene, gene expression, presence of gene product and/or amount of gene product, to a regression model (202) to determine and/or optimize parameters in the regression model thereby solving the regression model.

The regression model involves the HLX penalty as a combination of $L_{1/2}$ and $L_2$ penalties. Namely, the regression model can involve in this embodiment a linear combination of both $L_{1/2}$-regularized logistic regression and $L_2$-regularized logistic regression. The one or more processors (206) are further each arranged to process the biological data using the solved regression model (204) to determine one or more biological features (208) that are associated with the medical condition such as presence of one or more gene and its association with cancer or a specific subtype of cancer.

These processes, which can include methods of the present invention, may be implemented as a plurality of steps on a computer or computing device, such as those as found in FIG. 1.

Empirical results and simulations confirm that the system of the present invention provides several advantages over known approaches for feature selection. More specifically, empirical results and simulations show that the HLX regularization with involvement of both, $L_{1/2}$-regularized logistic regression and $L_2$-regularized logistic regression in the regression model, is highly competitive amongst usual approaches like Lasso, $L_{1/2}$, SCAD-$L_2$ and Elastic net in analyzing high dimensional and low sample sizes data like microarray and RNS-seq. data.

Thus, logistic regression with the HLX method represents a promising tool for feature selection in the classification problem.

The system of the present invention is in particular characterized by a new and advantageous HLX penalized function, which is in an embodiment a linear combination of $L_{1/2}$ and $L_2$ penalties, such as to select the relevant gene in the logistic regression. The HLX method inherits advantageous characteristics from the $L_{1/2}$ (sparsity) and $L_2$ (grouping effect where highly correlated variables are in or out a model together) penalties. Further, a novel univariate HLX thresholding approach is provided in embodiments to update the estimated coefficients and a coordinate descent process for the HLX penalized logistic regression model.

More specifically, a strictly convex penalty function provides a sufficient condition for the grouping effect of variables and the $L_2$ penalty guarantees strict convexity (Zeng L, Xie J, Statistics (Ber)., Taylor & Francis; 2014; 48: 49-66). Therefore, in the HLX regularization, the $L_{1/2}$ penalty advantageously achieves feature selection, and the $L_2$ penalty induces the grouping effect simultaneously.

Preferably but not exclusively, the system of the present invention can be used for determining an association of one or more of presence of a gene or genes, respective gene(s) expression, presence of a gene product or gene products and/or respective expression of gene product(s) with a medical condition like cancer or a specific subtype of cancer. In particular, the system of the present invention can be utilized for analyzing a dataset with biological data from humans including a plurality of gene expression levels.

Further features, applications and advantages of the method, the system and the non-transient computer readable medium for storing computer instructions according to the present invention will be evident for a person skilled in the art from the features and embodiments described below relating to a HLX regularization and a method for solving the logistic regression model.

In this embodiment, it is supposed that $X=[x_1|, \ldots, |x_p]$ is the matrix of n samples with p genes, $x_j=(x_{1j}, \ldots, x_{nj})^T$ for $j=1, \ldots, p$, and $y=(y_1, \ldots, y_n)^T$ is the corresponding response. For any non-negative $\lambda$, the normal regularization form is:

$$L(\lambda, \beta) = \operatorname{argmin} \frac{1}{n} \sum_{i=1}^{n} (y - X'\beta)^2 + \lambda P(\beta) \quad (1)$$

where $P(\beta)$ represents the regularization term. As mentioned before, there are many regularization methods proposed in recent years. One of popular method is the already described $L_1$ regularization (Lasso), where $$P(\beta) = \sum_{j=1}^{p} |\beta_j|^1.$$

The other $L_1$ type regularizations include SCAD, the adaptive Lasso, Elastic net, Stage wise Lasso (Zhao P, Yu B., J Mach Learn Res. JMLR. org; 2007; 8: 2701-2726), Dantzig selector (Candes E, Tao T., Ann Stat. JSTOR; 2007; 2313-2351) and Elastic SCAD. However, in genomic research, the result of the $L_1$ type regularization may not sparse enough for interpretation. Actually, a typical microarray or RNA-seq data set has many thousands of predictors (genes), researchers often desire to select fewer but informative genes. Beside this, the $L_1$ regularization is asymptotically biased (Knight K, Fu W., Ann Stat. JSTOR; 2000; 1356-1378, Malioutov D. et al., Signal Process IEEE Trans. IEEE; 2005; 53: 3010-3022). Although the $L_0$ regularization, where $$P(\beta) = \sum_{j=1}^{p} |\beta_j|^0,$$

yields the sparsest solutions, it has to deal with a NP hard combinatory optimization problem. To gain more concise solution and improve its predictive accuracy, one needs to think beyond the $L_1$ and $L_0$ regularization to the $L_q$ (0<q<1) regularization.

The $L_{1/2}$ regularization can be taken as a representative of the $L_q$ (0<q<1) penalties and has permitted an analytically expressive thresholding representation (Xu Z. et al., Sci China Inf Sci. Springer; 2010; 53: 1159-1169). With the thresholding representation, solving the $L_{1/2}$ regularization is much easier than solving the $L_0$ regularization. Moreover, the $L_{1/2}$ penalty is unbiasedness and has oracle properties (Xu Z. et al., Sci China Inf Sci. Springer; 2010; 53: 1159-1169, Zeng J. et al., Signal Process IEEE Trans. IEEE; 2014; 62: 2317-2329, Xu Z. et al., IEEE Trans neural networks Learn Syst. United States; 2012; 23: 1013-1027, doi: 10.1109/TNNLS.2012.2197412 [doi]).

These characteristics are making the $L_{1/2}$ penalty became an efficient tool for high dimensional problem (Liang Y. et al., BMC Bioinformatics. Faculty of Information Technology & State Key Laboratory of Quality Research in Chinese Medicines, Macau University of Science and Technology, Macau, China; 2013; 14: 198. doi:10.1186/1471-2105-14-198 [doi], Huang H-H. et al., Biomed Res Int. Hindawi Publishing Corporation; 2015). However, due to the insensitivity of the highly correlated data, the $L_{1/2}$ penalty tends to select only one variable represents the correlated group. This drawback may deteriorate the performance of the $L_{1/2}$ method.

For any fixed non-negative $\lambda_1$ and $\lambda_2$, the HLX criterion is defined:

$$L(\lambda_1, \lambda_2, \beta) = \operatorname{argmin} \frac{1}{n} \sum_{i=1}^{n} (y - X'\beta)^2 + \lambda_1 |\beta|^{1/2} + \lambda_2 |\beta|^2 \quad (2)$$

where $\beta=(\beta_1, \ldots, \beta_p)$ are the coefficients to be estimated and $$|\beta|^{1/2} = \sum_{j=1}^{p} |\beta_j|^{1/2},$$

$$|\beta|^2 = \sum_{j=1}^{p} |\beta_j|^2.$$

The HLX estimator $\hat{\beta}$ is the minimizer of Equation (2):

$$\hat{\beta} = \operatorname{arg\,min}_\beta \{L(\lambda_1, \lambda_2, \beta)\}. \quad (3)$$

Let $\alpha = \lambda_1/(1+\lambda_2)$, then solving $\hat{\beta}$ in Equation (3) is equivalent to the optimization problem:

$$\hat{\beta} = \operatorname{arg\,min}_\beta \{|y - X\beta|^2 + \lambda(\alpha|\beta|^{1/2} + (1-\alpha)|\beta|^2)\} \quad (4)$$

The function $\alpha|\beta|^{1/2} + (1-\alpha)|\beta|^2$ is called the HLX penalty, which is a combination of the $L_{1/2}$ and $L_2$ penalties. When $\alpha=0$, the HLX penalty becomes ridge regularization. When $\alpha=1$, the HLX penalty becomes $L_{1/2}$ regularization. The $L_2$ penalty is enjoying the grouping effect and the $L_{1/2}$ induces sparse solutions. This penalty combination makes the HLX regularization not only capable of dealing with the correlation data but also able to generate a succinct result.

In FIGS. 3A to 3D four regularization methods are shown: Lasso, $L_{1/2}$, Elastic net and HLX penalties with an orthogonal design matrix in the regression model. The estimators of Lasso and Elastic net are biased, whereas $L_{1/2}$ is asymptotically unbiased. Similar to $L_{1/2}$, the new HLX approach also performs better than Lasso and Elastic net in the property of unbiasedness.

Figure 4:
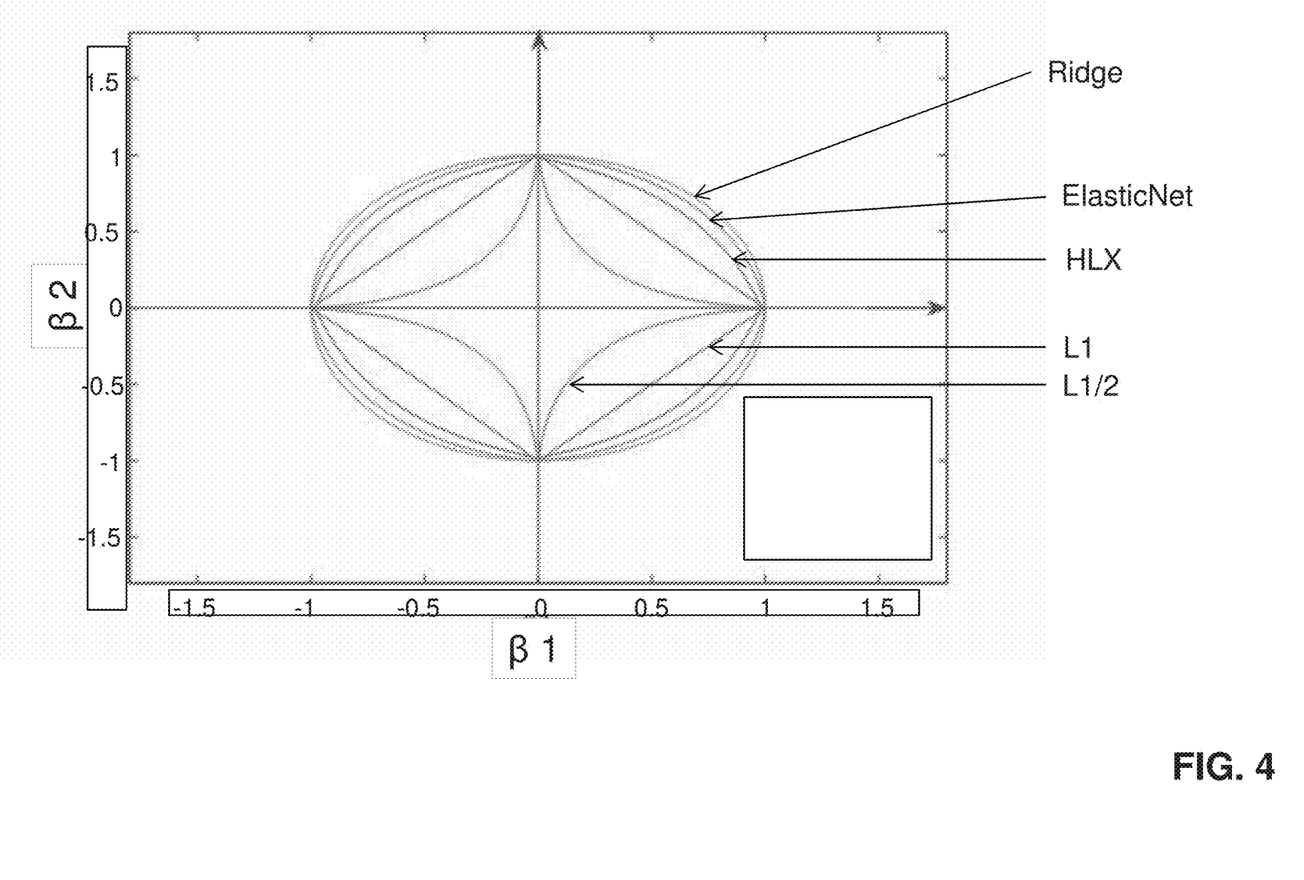
FIG. 4 refers to contour plots (two dimensional) for the regularization methods. The regularization parameters are $\lambda=1$ and $\alpha=0.2$ for the HLX method.

In FIG. 4 the contour plots on two dimensional for the penalty functions of Lasso, Elastic net, $L_{1/2}$ and new HLX approaches are described. It is clear that the $L_{1/2}$ penalty is non-convex, whereas the HLX penalty is convex for the given $\alpha$. The following theorem will show how the HLX regularization strengthens the $L_{1/2}$ regularization.

Theorem 1. Given dataset (y, X) and $(\lambda_1, \lambda_2)$, then the HLX estimates $\hat{\beta}$ are given by $$\hat{\beta} = \operatorname{argmin}_\beta \beta^T \left( \frac{X^T X + \lambda_2 I}{1 + \lambda_2} \right) \beta - 2y^T X \beta + \lambda_1 |\beta|^2. \quad (5)$$

The $L_{1/2}$ regularization can be rewritten as $$\hat{\beta}(L_{1/2}) = \operatorname{arg\,min}_\beta \beta^T (X^T X) \beta - 2y^T X \beta + \lambda_1 |\beta|^{1/2}. \quad (6)$$

The proof of theorem 1 is similar to that in Zou and Hastie (J R Stat Soc Ser B, Statistical Methodol. Wiley Online Library; 2005; 67: 301-320).

Lemma 1. Given dataset (y, X) and $(\lambda_1, \lambda_2)$, define an artificial dataset (y*, X*) by $$X^*_{(n+p) \times p} = (1 + \lambda_2)^{-\frac{1}{2}} \left( \frac{X}{\sqrt{\lambda_2} I} \right), \quad Y^*_{(n+p)} = \binom{Y}{0}.$$

Let $\gamma = \lambda_1 / \sqrt{1+\lambda_2}$ and $\beta^* = \sqrt{1+\lambda_2}\, \beta$ Then the HLX criterion can be expressed as)

$$L(\lambda_1, \lambda_2, \beta) = L(\gamma, \beta^*) = |y^* - X^*\beta^*|^2 + \gamma |\beta^*|_{1/2}$$

Let $$\beta^* = \operatorname{arg\,min}_\beta \{L(\gamma, \beta^*)\},$$

Then $$\hat{\beta} = (1/\sqrt{1+\lambda_2})\hat{\beta}^*.$$

Assume $\hat{\beta}$ is the estimates for the HLX regularization. By Lemma 1 and equation (2) we have $$\hat{\beta} = \operatorname{argmin}_\beta \left| y^* - X^* \frac{\beta}{\sqrt{1+\lambda_2}} \right|^2 + \frac{\lambda_1}{\sqrt{1+\lambda_2}} \left| \frac{\beta}{\sqrt{1+\lambda_2}} \right|_{1/2} \quad (13)$$

$$= \operatorname{argmin}_\beta \beta^T \left( \frac{X^{*T}X^*}{1+\lambda_2} \right) \beta - 2\frac{y^{*T}X^*\beta}{\sqrt{1+\lambda_2}} + y^{*T}y^* + \frac{\lambda_1|\beta|_{1/2}}{1+\lambda_2}.$$

Substituting the identities $$X^{*T}X^* = \left( \frac{X^T X + \lambda_2}{1+\lambda_2} \right),$$

$$y^{*T}X^* = \left( \frac{y^T X}{\sqrt{1+\lambda_2}} \right),$$

$$y^{*T}y^* = y^T y$$

into equation (13), we have $$\hat{\beta} = \operatorname{argmin}_\beta \frac{1}{1+\lambda_2} \left\{ \beta^T \left( \frac{X^T X + \lambda_2 I}{1+\lambda_2} \right) \beta - 2 y^T X \beta + \lambda_1 |\beta|_{1/2} \right\} + y^T y$$

$$= \operatorname{argmin}_\beta \beta^T \left( \frac{X^T X + \lambda_2 I}{1+\lambda_2} \right) \beta - 2 y^T X \beta + \lambda_1 |\beta|_{1/2}.$$

Theorem 1 shows the new HLX approach is a stabilized version of the $L_{1/2}$. Note that $\hat{\Sigma}=X^T X$ is a sample version of the correlation matrix $\Sigma$ and $$\frac{X^T X + \lambda_2 I}{1+\lambda_2} = (1-\delta)\hat{\Sigma} + \delta I$$

With $\delta = \lambda_2/(1+\lambda_2)$ shrinks $\hat{\Sigma}$ towards the identity matrix.

The classification accuracy can often be enhanced by replacing $\hat{\Sigma}$ by a more shrunken estimate in linear discriminate analysis (Friedman J H., J Am Stat Assoc. Taylor & Francis; 1989; 84: 165-175, Hastie T. et al., Math Intell. Springer; 2005; 27: 83-85). In other word, the HLX regularization improves the $L_{1/2}$ technique by regularizing $\hat{\Sigma}$ in Equation (6).

For sparse Logistic Regression with the HLX regularization it is supposed that dataset D has n samples $D=\{(X_1, y_1), (X_2, y_2), \ldots (X_n, y_n)\}$, where $X_i=(x_{i1}, x_{i2}, \ldots, x_{ip})$ is $i^{th}$ sample with p genes and $y_i$ is the corresponding dependent variable that consist of a binary value with 0 or 1. Define a classifier $f(x)=e^x/(1+e^x)$ and the logistic regression is defined as:

$$P(y_i = 1 \mid X_i) = f(X_i'\beta) = \frac{\exp(X_i'\beta)}{1+\exp(X_i'\beta)} \quad (7)$$

where $\beta=(\beta_1, \ldots, \beta_p)$ are the coefficients to be estimated. The regression model can, thus, be presented as:

$$L(\beta) = -\sum_{i=1}^{n} \{y_i \log[f(X_i'\beta)] + (1-y_i)\log[1-f(X_i'\beta)]\} \quad (8)$$

In the present invention, HLX penalty is applied to the logistic regression model. For any fixed non-negative $\lambda$ and $\alpha$, the sparse logistic regression model based on the HLX regularization is defined in embodiments of the present invention as:

$$L(\lambda, \alpha, \beta) = -\sum_{i=1}^{n} \{y_i \log[f(X_i'\beta)] + (1-y_i)\log[1-f(X_i'\beta)]\} + \quad (9)$$
$$\lambda(\alpha|\beta|^{1/2} + (1-\alpha)|\beta|^2)$$

Solution for Logistic Regression with the HLX regularization: The coordinate descent method (Friedman J. et al., J Stat Softw. NIH Public Access; 2010; 33: 1) is an efficient method for solving regularization models. The computational time increases linearly with the dimension p, make this method particularly fit for solving high-dimensional problems (Breheny P, Huang J., Ann Appl Stat. NIH Public Access; 2011; 5: 232). Its standard procedure can be showed as follows: for every $\beta_j (j=1, 2, \ldots, p)$, to partially optimize the target function with respect to coefficient with the remaining elements of $\beta$ fixed at their most recently updated values, iteratively cycling through all coefficients until meet converged.

The specific form of renewing coefficients is associated with the thresholding operator of the penalty. Following Friedman et al. (Friedman J. et al., J Stat Softw. NIH Public Access; 2010; 33: 1) and Liang et al. (Liang Y, et al., BMC Bioinformatics. Faculty of Information Technology & State Key Laboratory of Quality Research in Chinese Medicines, Macau University of Science and Technology, Macau, China; 2013; 14: 198, doi:10.1186/1471-2105-14-198 [doi]), in this invention, a coordinate-wise update form for the HLX penalty is presented:

$$\beta_j \leftarrow \frac{\text{Half}(\omega_j, \lambda\alpha)}{1+\lambda(1-\alpha)} \quad (10)$$

Where $\omega_j = \sum_{i=1}^{n} x_{ij}(y_i - \tilde{y}_i^{(j)})$ and $\tilde{y}_i^{(j)} = \sum_{k \neq j} x_{ik}\beta_k$ as the partial residual for fitting $\beta_j$. Half $(z, r)$ is the $L_{1/2}$ thresholding operator $$\text{Half}(\omega_j, \lambda) = \begin{cases} \frac{2}{3}\omega_j \left( 1 + \cos\left( \frac{2(\pi - \varphi_\lambda(\omega_j))}{3} \right) \right) & \text{if } |\omega_j| > \frac{3}{4}(\lambda)^{\frac{2}{3}} \\ 0 & \text{otherwise} \end{cases} \quad (11)$$

where $\varphi_\lambda(\omega) = \arccos\left( \frac{\lambda}{8}\left( \frac{|\omega|}{3} \right)^{-\frac{3}{2}} \right)$, $\pi = 3.14$.

The Equation (9) can be linearized by one-term Taylor series expansion:

$$L(\lambda, \alpha, \beta) \approx \frac{1}{2n}\sum_{i=1}^{n}(Z_i - X_i\beta)'W_i(Z_i - X_i\beta) + \lambda(\alpha|\beta|^{1/2} + (1-\alpha)|\beta|^2) \quad (12)$$

where $Z_i = X_i\tilde{\beta} + \frac{y_i - f(X_i\tilde{\beta})}{f(X_i\tilde{\beta})(1-f(X_i\tilde{\beta}))}$ is the estimated response, $W_i=f(X_i\tilde{\beta})(1-f(X_i\tilde{\beta}))$ is the weight for the estimated response. $f(X_i\tilde{\beta})=\exp(X_i\tilde{\beta})/(1+\exp(X_i\tilde{\beta}))$ is evaluated value under the current parameters. Thus, we can redefine the partial residual for fitting current $\tilde{\beta}$ as $$\tilde{Z}_i^{(j)} = \sum_{k \neq j} x_{ik}\tilde{\beta}_k \text{ and } \omega_j = \sum_{i=1}^{n} W_i x_{ij}\left(Z_i - \tilde{Z}_i^{(j)}\right).$$

A procedure of the coordinate descent method for the HLX penalized logistic model is described as follows.

A coordinate descent method for the HLX penalized logistic model:

Step 1: Initialize all $\beta_j(m) \leftarrow 0$ ($j=1, 2, \ldots, p$) and X, y, set $m \leftarrow 0$, $\lambda$ and $\alpha$ are chosen by cross-validation;

Step 2: Calculate $Z(m)$ and $W(m)$ and approximate the loss function (12) based on the current $\beta(m)$;

Step 3: Update each $\beta_j(m)$, and cycle over $j=1, \ldots, p$

Step 3.1: Compute $_i^{(j)}(m) \leftarrow \Sigma_{k \neq j} x_{ik}\beta_k(m)$ and $$\omega_j(m) \leftarrow \sum_{i=1}^{n} W_i(m)x_{ij}\left(Z_i(m) - \tilde{Z}_i^{(j)}(m)\right);$$

Step 3.2: Update $$\beta_j(m) \leftarrow \frac{\text{Half }(\omega_j(m), \lambda\alpha)}{1 + \lambda(1 - \alpha)};$$

Step 4: Let $m \leftarrow m+1$, $\beta(m+1) \leftarrow \beta(m)$;

If $\beta(m)$ dose not convergence, then repeat Steps 2, 3

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the present invention are either wholly implemented by computing system or partly implemented by computing systems then any appropriate computing system architecture may be utilized. This will include standalone computers, network computers and dedicated hardware devices. Where the terms "computing system" and "computing device" are used, these terms are intended to cover any appropriate arrangement of computer hardware capable of implementing the function described.

It will be appreciated by persons skilled in the art that the term "database" may include any form of organized or unorganized data storage devices implemented in either software, hardware or a combination of both which are able to implement the function described.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

EXAMPLES

Example 1

Analyses of Simulated Data

The goal was to evaluate the performance of logistic regression with the HLX regularization in the simulation study.

Four approaches were compared with the approach according to the present invention: logistic regression with the Lasso regularization, $L_{1/2}$ regularization, SCAD-$L_2$ and Elastic net regularization respectively. The data have been simulated from the true model $$\log\left(\frac{y}{1-y}\right) = X\beta + \sigma\epsilon, \epsilon \sim N(0, 1).$$

Where $X \sim N(0,1)$, $\in$ is the independent random error and $\sigma$ is the parameter which controls the signal to noise. Three scenarios are presented here. In every example, the dimension of predictors was 2000. The notation ./. represents the number of observations in the training and test sets respectively, e.g. 100/100. Here are the details of the three scenarios.

(a) In scenario 1, the dataset consisted of 100/100 observations, $\sigma$ was set=0.3 and $$\beta = (\underbrace{2, 2, 2, 2, 2}_{5}, \underbrace{0, \ldots, 0}_{1995}).$$

A grouped variable situation has been simulated $x_i = \rho \times x_1 + (1-\rho) \times x_i, i=2,3,4,5.$ where $\rho$ is the correlation coefficient of the grouped variables.

(b) The scenario 2 was defined similarly to scenario 1, except that the case when there are other independently factors also contributes to the y has been considered $$\beta = (\underbrace{2, 2, 2, 2, 2}_{5}, \underbrace{0, \ldots, 0}_{5}, \underbrace{1.5, -2, 1.7, 3, -2.5}_{5}, \underbrace{0, \ldots, 0}_{1985}).$$

(c) In scenario 3, $\sigma$ was set=0.4 and the dataset consisted of 200/200 observations, and $$\beta = (\underbrace{2, 2, 2, 2, 2}_{5}, \underbrace{0, \ldots, 0}_{5}, \underbrace{1.5, -2, 1.7, 3, -2.5}_{5|},$$

$$\underbrace{0, \ldots, 0}_{5}, \underbrace{3, 3, 3, 3, 3}_{5}, \underbrace{0, \ldots, 0}_{5}, \underbrace{3, 3, 3, -3, -2}_{5}, \underbrace{0, \ldots, 0}_{1965}).$$

Two grouped variables have been defined $x_i = \rho \times x_1 + (1-\rho) \times x_i, i=2,3,4,5;$ $x_i = \rho \times x_{21} + (1-\rho) \times x_i, i=22,23,24,25.$ In this example, there were four important groups, and within each group there have been five members, correlated or independent. An ideal method would select only the 20 true features and set the coefficients of the 1980 noise features to zero.

true features compared to the other four methods. For example, in the scenario 1 with p=0.9, the method of the present invention gained impressive performance (Accuracy 99.63% with perfect Sensitivity and perfect Specificity). The specificity was somewhat decreased, but not greatly as compared to the achieved in sensitivity.

TABLE 1

Results of the simulation. In bold - the best (or one of the best) performance

| | | Scenario | | | | | | | | |
|---|---|---|---|---|---|---|---|---|---|---|
| | | 1 | 2 | 3 | 1 | 2 | 3 | 1 | 2 | 3 |
| p | Methods | Sensitivity | | | Specificity | | | Accuracy | | |
| 0.3 | Lasso | 0.948 | 0.540 | 0.238 | 0.995 | 0.989 | 0.991 | 91.40% | 68.90% | 65.26% |
| | $L_{1/2}$ | 1.000 | 0.700 | 0.655 | 0.998 | 0.997 | 0.975 | 92.00% | 73.40% | 70.40% |
| | SCAD-$L_2$ | 1.000 | 0.757 | 0.600 | 0.999 | 0.971 | 0.923 | 92.70% | 72.90% | 67.51% |
| | EN | 0.973 | 0.772 | 0.740 | 0.994 | 0.975 | 0.844 | 90.00% | 70.40% | 64.47% |
| | HLX | 1.000 | 0.792 | 0.793 | 0.999 | 0.985 | 0.934 | 93.53% | 75.54% | 68.20% |
| 0.6 | Lasso | 0.724 | 0.453 | 0.280 | 0.997 | 0.995 | 0.993 | 95.50% | 77.43% | 74.20% |
| | $L_{1/2}$ | 0.400 | 0.400 | 0.440 | 0.999 | 0.997 | 0.976 | 96.30% | 78.62% | 75.30% |
| | SCAD-$L_2$ | 1.000 | 0.770 | 0.620 | 1.000 | 0.960 | 0.948 | 98.90% | 79.50% | 77.20% |
| | EN | 1.000 | 0.720 | 0.766 | 0.988 | 0.979 | 0.861 | 97.20% | 74.53% | 69.20% |
| | HLX | 1.000 | 0.802 | 0.698 | 1.000 | 0.989 | 0.947 | 99.30% | 82.68% | 76.30% |
| 0.9 | Lasso | 0.436 | 0.276 | 0.173 | 0.999 | 0.996 | 0.995 | 98.32% | 85.16% | 77.66% |
| | $L_{1/2}$ | 0.200 | 0.400 | 0.360 | 1.000 | 0.998 | 0.996 | 98.33% | 88.01% | 79.00% |
| | SCAD-$L_2$ | 1.000 | 0.690 | 0.675 | 0.999 | 0.984 | 0.918 | 99.60% | 82.70% | 80.60% |
| | EN | 0.995 | 0.810 | 0.731 | 0.999 | 0.978 | 0.877 | 98.80% | 83.90% | 74.70% |
| | HLX | 1.000 | 0.830 | 0.745 | 1.000 | 0.980 | 0.911 | 99.63% | 82.60% | 85.70% |

In this example, correlation coefficient was set ρ=0.3, 0.6, 0.9 respectively. The Lasso and Elastic net were conducted by Glmnet (a Matlab package, version 2014-04-28, download at http://web.stanford.edu/~hastie/glmnet_matlab/). The regularization parameters of the Lasso, $L_{1/2}$, SCAD-$L_2$, Elastic net and the HLX approaches were tuned by 10-fold cross validation (CV) in the training set. The Elastic net and HLX methods were tuned by 10-CV on the two dimensional parameter surfaces. The SCAD-$L_2$ has three parameters (α, $\lambda_1$ and $\lambda_2$), and α was set=2, 2.25, 2.5, 3, 3.5, 3.7, respectively, $\lambda_1$ and $\lambda_2$ were also tuned by 10-CV on the two dimensional parameter surfaces.

The simulations were repeated 100 times and the classification accuracy was computed on the test sets. To evaluate the quality of the selected features, the sensitivity and specificity of variable selection performance (Zhang W. et al., BMC Genomics. England; 2013; 14 Suppl 8: S7-2164-14-S8-S7. Epub 2013 Dec. 9. doi:10.1186/1471-2164-14-S8-S7 [doi]) was defined as follows:

$$\text{True Negative}(TN) := \left| \bar{\beta}.*\bar{\hat{\beta}} \right|_0, \text{False Positive}(FP) := \left| \bar{\beta}.*\hat{\beta} \right|_0$$

$$\text{False Negative}(FN) := \left| \beta.*\bar{\hat{\beta}} \right|_0, \text{True Positive}(TP) := \left| \beta.*\hat{\beta} \right|_0$$

$$\text{Sensitivity} := \frac{TP}{TP+FN}, \text{Specificity} := \frac{TN}{TN+FP}.$$

where the .* is the element-wise product and $|.|_0$ calculates the number of non-zero elements in a vector, $\bar{\beta}$ is the logical "not" operator on a vector.

For all scenarios, in general, the HLX procedure proposed with the present invention and embodiments thereof gave higher or comparable accuracy than the Lasso, SCAD-$L_2$, Elastic net and $L_{1/2}$ methods (Table 1). In addition, the HLX penalty resulted in much higher sensitivity in identifying Example 2

Analyses of Real Data

Three publicly available datasets have been used: Prostate, DLBCL and Lung cancer, to further evaluate the effectiveness of the method of the present invention. The Prostate, DLBCL datasets were downloaded from http://ico2s.org/datasets/microarray.html, and the Lung cancer dataset can be downloaded at www.ncbi.nlm.nih.gov/geo with access number [GSE40419]. A brief description of these three datasets is given below and summarized in Table 2.

Prostate: This dataset was originally proposed by Singh et al. (Singh D, et al., Cancer Cell. Elsevier; 2002; 1: 203-209); it is containing the expression profiles of 12,600 genes for 50 normal tissues and 52 prostate tumor tissues. Glaab E. et al. (PLoS One. Public Library of Science; 2012; 7: e39932) has been followed to preprocess the data.

Lymphoma: This dataset (Shipp et al. (Shipp M A. et al., Nat Med. Nature Publishing Group; 2002; 8: 68-74) contains 77 microarray gene expression profiles of the 2 most prevalent adult lymphoid malignancies: 58 samples of diffuse large B-cell lymphomas (DLBCL) and 19 follicular lymphomas (FL). The original data contains 7, 129 gene expression values. Glaab E. et al. (PLoS One. Public Library of Science; 2012; 7: e39932) has been followed to preprocess the data.

Lung cancer: As RNA-sequencing (RNA-seq) technique widely used, therefore, it is important to test the proposed method whether it has the ability to handle the RNA-seq data. To verify it, one dataset which used the next-generation sequencing was involved in our analysis. This dataset (Seo J S. et al., Genome Res. Genomic Medicine Institute (GMI), Medical Research Center, Seoul National University, Seoul 110-799, Korea; 2012; 22: 2109-2119. doi:10.1101/gr.145144.112 [doi]) contains 164 samples with 87 lung adenocarcinomas and 77 adjacent normal tissues. We followed Seo J S. et al. (Genome Res. Genomic Medicine Institute (GMI), Medical Research Center, Seoul National University, Seoul 110-799, Korea; 2012; 22: 2109-2119. doi:10.1101/gr.145144.112 [doi]) to preprocess the data.

TABLE 2

Datasets used in this example.

| Dataset | No. of samples | No. of genes | Classes |
|---|---|---|---|
| Prostate | 102 | 12600 | Normal/Tumor |
| Lymphoma | 77 | 7129 | DLBCL/FL |
| Lung cancer | 164 | 22401 | Normal/Tumor |

Each of three datasets was randomly partitioned into training set (70%~80%) and test set (20%~30%). More information on these datasets is given in Table 3.

TABLE 3

Three gene expression datasets used in this example.

| Dataset | No. of Training | No. of Testing |
|---|---|---|
| Prostate | 77 | 25 |
| Lymphoma | 57 | 20 |
| Lung cancer | 124 | 40 |

The training and the test classification accuracy has been calculated. The performance of area under the curve (AUC) based on receiver operating characteristic (ROC) analysis for the test set was also recorded. The parameter(s) of the regularization methods were tuning by 10-fold CV in one or two dimensions. This procedure has been repeated 50 times, the averaged classification results (training accuracy based on 10-fold CV and accuracy in test set) were summarized in Table 4 and the averaged ROC analysis results are shown in FIG. 5.

As shown in Table 4, for Prostate dataset, the classifier with the HLX regularization gave an average 10-fold CV accuracy of 97.50% and an average test accuracy of 93.88% with about 11 genes selected. The classifiers with Lasso, $L_{1/2}$, SCAD-$L_2$ and Elastic net methods gave an average 10-fold CV accuracy of 96.09%, 96%, 96.09%, 96.25% and an average test accuracy of 92.08%, 92.08%, 91.31%, 92.40% with about 12, 7, 21 and 15 genes selected respectively. For lymphoma and lung cancer datasets, in general, it can be seen the HLX penalty achieved the best classification performances with the highest accuracy rates in the training and test sets.

Figure 5:
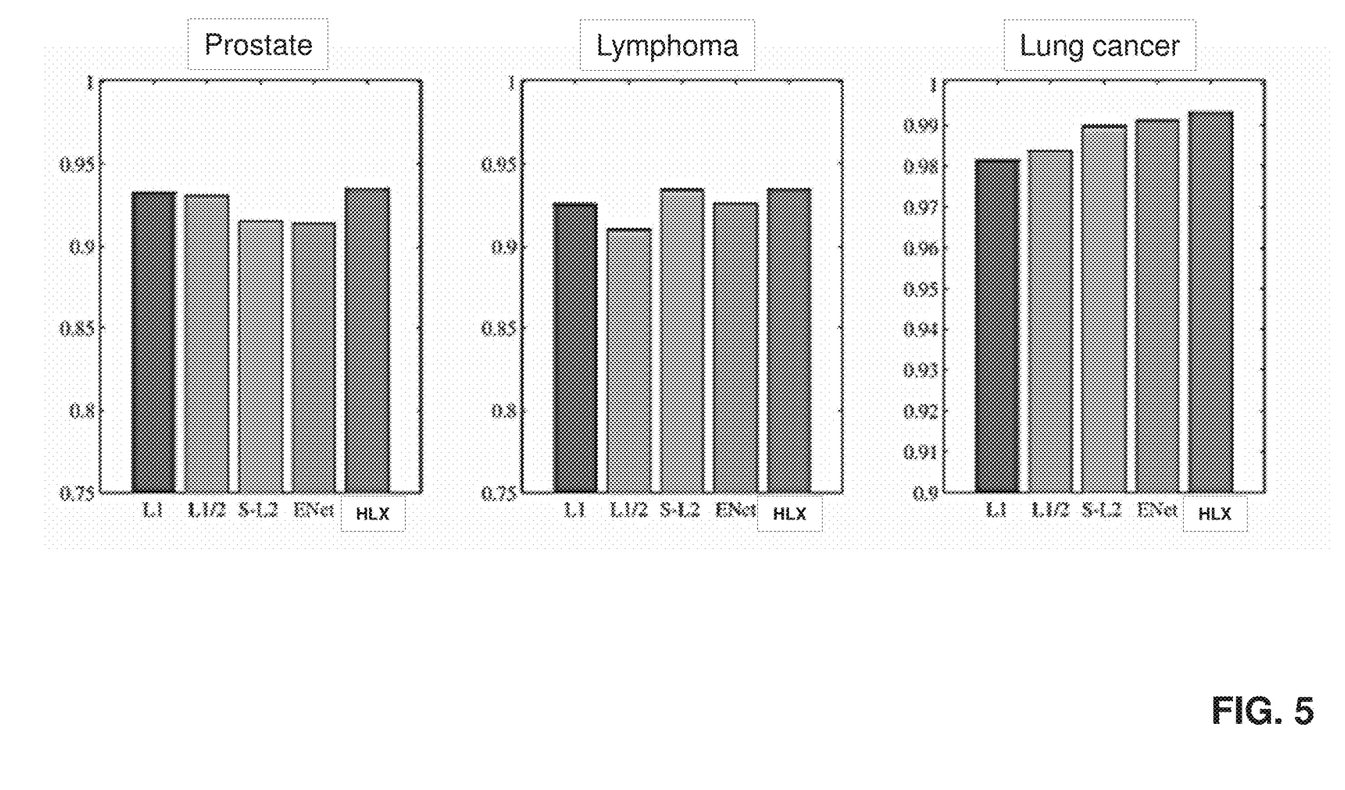
FIG. 5 illustrates the performance of the AUC from ROC analyses of each method on every dataset of example 2.

As shown in FIG. 5, with a method of the present invention the best classification performances in these three datasets amongst all the competitors can be achieved. For example, the AUC from ROC analysis of the HLX method for datasets prostate, lymphoma and lung cancer were estimated to be 0.9383, 0.9314 and 0.9928 respectively. AUC results of the Lasso method for the three datasets were calculated to be 0.9315, 0.9263 and 0.9809 respectively, which were worse than with a method of the present invention.

TABLE 4

Result of empirical datasets. In bold - the best performance

| Dataset | Method | Training accuracy (10-CV) | Accuracy (testing) | No. of selected genes |
|---|---|---|---|---|
| Prostate | Lasso | 96.09% | 92.08% | 12 |
|  | $L_{1/2}$ | 96.00% | 92.08% | 7 |
|  | SCAD-$L_2$ | 96.09% | 91.31% | 21 |
|  | ElasticNet | 96.25% | 92.40% | 15 |
|  | HLX | 97.50% | 93.88% | 11 |
| Lymphoma | Lasso | 96.33% | 91.00% | 18 |
|  | $L_{1/2}$ | 95.25% | 91.40% | 14 |
|  | SCAD-$L_2$ | 96.10% | 93.67% | 24 |
|  | ElasticNet | 95.98% | 92.00% | 31 |
|  | HLX | 96.39% | 93.83% | 16 |
| Lung cancer | Lasso | 97.46% | 98.33% | 10 |
|  | $L_{1/2}$ | 98.38% | 97.50% | 9 |
|  | SCAD-$L_2$ | 97.85% | 98.29% | 25 |
|  | ElasticNet | 97.18% | 98.38% | 24 |
|  | HLX | 98.63% | 98.33% | 15 |

The top 10 ranked genes selected by the four regularization methods for the lung cancer gene expression dataset are summarized in Table 5, the information of top 10 ranked genes for the other datasets are presented in Tables 6 and 7.

Considering that a method of the present invention allowed for the best performances to select the true features in the simulation (Table 1), it is implied that the genes selected by the HLX method in these three cancer datasets are valuable to the researchers who the goal is to find out the key factors that associated with the cancer development. For example, in Table 5, the biomarkers selected with a method of the present invention include advanced glycosylation end product receptor (AGER), which is a member of the immunoglobulin superfamily predominantly expressed in the lung. AGER plays a role in epithelial organization, and decreased exxression of AGER in lung tumors may conduce to loss of epithelial tissue structure, potentially leading to malignant transformation (Bartling B. et al., Carcinogenesis. Clinic of Cardiothoracic Surgery, Martin Luther University Halle-Wittenberg, Ernst-Grube-Strasse 40, D-06120 Halle/Saale, Germany; 2005; 26: 293-301. doi:bgh333 [pii]). The unique function of AGER in lung indicate that it could be used as an additional diagnostic tool for lung cancer (Buckley S T, Ehrhardt C., J Biomed Biotechnol. School of Pharmacy and Pharmaceutical Sciences, Trinity College Dublin, Dublin 2, Ireland.; 2010; 2010: 917108. doi: 10.1155/2010/917108 [doi]), and even as a target (Jing R. et al., Neoplasma. Center of Laboratory Medicine, Affiliated Hospital of Nantong University, Affiliated Hospital of Nantong University, 20 Xi Si Road, Nantong 226001, PR China; 2010; 57: 55-61). Neutrophil cytosolic factor 1 (NCF1), the regulatory subunit of NADPH oxidase:

The expression profile of NCF1 was associated with lung cancer development (Kelkka T. et al., PLoS One. Public Library of Science; 2013; 8:e84148.doi:10.1371/journal-.pone.0084148, Vuong H. et al., Genome Med. Department of Biomedical Informatics, Vanderbilt University School of Medicine, 2525 West End Avenue, Suite 600, Nashville, Tenn. 37203 USA; Department of Biomedical Informatics, Vanderbilt University School of Medicine, 2525 West End Avenue, Suit (2014; 6: 81-014-0081-7. eCollection 2014. doi:10.1186/s13073-014-0081-7 [doi])).

Moreover, interestingly, there were at least two groups within the 10 top-rank genes selected by HLX. For example, the correlation coefficients between the expression of AGER and ABCA8, EIF4E1B and CXXC1P1 were calculated to be 0.5 and 0.8, respectively. They were successfully selected as group variables with a method of the present invention.

TABLE 5

The 10 top-ranked informative genes found by the five sparse logistic regression methods from the Lung cancer dataset.

| Rank | Lasso | $L_{1/2}$ | SCAD-$L_2$ | ElasticNet | HLX |
|---|---|---|---|---|---|
| 1 | KRTAP4-6 | A2M | SCUBE1 | ERI2 | AGER |
| 2 | FAM150B | A4GNT | MIR548Y | C16orf70 | ABCA8 |
| 3 | RADIL | ABCA8 | CAV1 | AGER | LGI3 |
| 4 | MIR548Y | AATK | C15orf32 | IL1F9 | MIR548Y |
| 5 | PHYHIPL | B9D2 | ID3 | CBLN4 | MIR98 |
| 6 | LGI3 | BDKRB1 | TNXB | KRTAP4-6 | NCF1 |
| 7 | AKAP2 | PNLIP | PHYHIPL | SIK2 | C10orf54 |
| 8 | ID3 | CDON | KCNT2 | RADIL | EIF4E1B |
| 9 | SCUBE1 | CASQ1 | CCL19 | FABP5 | CXXC1P1 |
| 10 | TNXB | CD244 | ARHGAP44 | CFD | CYP17A1 |

TABLE 6

The most frequently selected 10 genes found by the five sparse logistic regression methods from the prostate dataset.

| Rank | Lasso | $L_{1/2}$ | SCAD-$L_2$ | ElasticNet | HLX |
|---|---|---|---|---|---|
| 1 | PTDSS1 | PTGDS | ATP5I | PTDSS1 | HPN |
| 2 | ATP5I | JUNB | TP63 | G0S2 | DUSP1 |
| 3 | S100A4 | RP11-124D2.7 | PTDSS1 | S100A4 | NTRK1 |
| 4 | AGR2 | POLR2M | AGR2 | TP63 | GSTA2 |
| 5 | XBP1 | CYBA | MYOF | XBP1 | TP63 |
| 6 | HPN | RRAD | D4S234E | JUNB | NELL2 |
| 7 | PTGDS | NR4A3 | S100A4 | C1QTNF3-AMACR | PTDSS1 |
| 8 | SDC1 | CTSG | PRKCB | FP236383.12 | SERINC5 |
| 9 | JUNB | PRKCB | CTSG | SERPINA3 | PHLDA2 |
| 10 | CFD | ATP5I | ME1 | JUND | ATP5I |

TABLE 7

The most frequently selected 10 genes found by the five sparse logistic regression methods from the lymphoma dataset.

| Rank | Lasso | $L_{1/2}$ | SCAD-$L_2$ | ElasticNet | HLX |
|---|---|---|---|---|---|
| 1 | TLN2 | TLN2 | ESPL1 | GANAB | UPK2 |
| 2 | ARID4B | IFNA2 | UPK2 | NUP93 | TLN2 |
| 3 | BRD2 | IGLV4-3 | IFFO1 | MIR4668 | CCL21 |
| 4 | IFFO1 | CSTA | PRDX6 | UPK2 | RRS1 |
| 5 | RPL24 | DLGAP5 | IFNA1 | OMD | IFFO1 |
| 6 | PRDX6 | CCL21 | PNP | TLN2 | CIRBP |
| 7 | CCL21 | IFNA1 | IGHEP1 | CCL21 | PSMA4 |
| 8 | RP11-419C5.2 | BRD2 | CCL21 | CYP4F3 | CCR1 |
| 9 | UPK2 | ADIPOQ | KDR | RPL24 | RPL24 |
| 10 | CIRBP | ESPL1 | DTYMK | PRDX6 | GANAB |

In addition to comparing with the Lasso, $L_{1/2}$, SCAD-$L_2$ and Elastic net techniques, a comparison with the results of other methods published in the literature has been consucted. Only methods were considered using CV for evaluation, since approaches based on a mere training/test set partition are now widely known as unreliable (Ambroise C, McLachlan G J., Proc Natl Acad Sci USA. Laboratoire Heudiasyc, Unite Mixte de Recherche/Centre National de la Recherche Scientifique 6599, 60200 Compiegne, France.; 2002; 99: 6562-6566. doi:10.1073/pnas.102102699 [doi]).

Table 6 displays the best classification accuracy of other methods. In Table 6, classification accuracy achieved by the HLX regularization approach is greater than other methods meanwhile the number of selected genes is significantly smaller than other methods except on the Lymphoma dataset.

TABLE 6

Result of the literatures. In bold - the best performance*

| Dataset | Authors | Accuracy (CV) | No. of selected features |
|---|---|---|---|
| Prostate | T.K. Paul et al. [33] | 96.60% | 48.5 |
| | Wessels et al. [34] | 93.40% | 14 |
| | Shen et al. [35] | 94.60% | unknown |
| | Lecocke et al. [36] | 90.10% | unknown |
| | Dagliyan et al. [37] | 94.80% | unknown |
| | Glaab et al. [24] | 94.00% | 30 |
| | HLX | 97.50% | 11 |
| Lymphoma | Wessels et al. [34] | 95.70% | 80 |
| | Liu et al. [38] | 93.50% | 6 |
| | Shipp et al. [25] | 92.20% | 30 |
| | Goh et al. [39] | 91.00% | 10 |
| | Lecocke et al. [36] | 90.20% | unknown |
| | Hu et al. [40] | 87.01% | unknown |
| | Dagliyan et al. [37] | 92.25% | unknown |
| | Glaab et al. [24] | 95.00% | 30 |
| | HLX | 96.39% | 16 |

*[33] Paul T K, Iba H., ACM; 2005. pp. 453-460,
[34] Wessels L F. et al., Bioinformatics. Department of Mediamatics, Faculty of Electrical Engineering, Mathematics and Computer Science, Delft University of Technology Mekelweg 4, 2628 CD Delft, The Netherlands; 2005; 21: 3755-3762. doi: bti429 [pii],
[35] Shen L., Tan E C., IEEE/ACM Trans Comput Biol Bioinforma. IEEE Computer Society Press; 2005; 2: 166-175,
[36] Lecocke M., Hess K., Cancer Inform. Department of Mathematics, St. Mary's University, San Antonio, Texas 78228, USA.; 2007; 2: 313-327,
[37] Dagliyan O. et al., PLoS One. Department of Chemical and Biological Engineering, Koc University, Istanbul, Turkey.; 2011; 6: e14579. doi: 10.1371/journal.pone.0014579 [doi],
[38] Liu J., Zhou H., Machine Learning and Cybernetics, 2003 International Conference on. IEEE; 2003. pp. 2275-2280,
[39] Goh L. et al., Proceedings of the second conference on Asia-Pacific bioinformatics-Volume 29. Australian Computer Society, Inc.; 2004. pp. 161-166,
[40] Hu Y., Kasabov N., Neural Information Processing. Springer; 2008. pp. 846-855.

The invention claimed is:

1. A method for determining association of gene-related biological features with cancer, the method comprising the steps of:

processing, using one or more processors, at least some biological data in a dataset using a regression model to determine or optimize parameters in the regression model thereby solving the regression model, the biological data being related to a plurality of samples taken from humans at least some of which have the cancer, each of the plurality of samples including a plurality of gene-related biological features of the following type: presence of a gene, gene expression, presence of a gene product, or amount of a gene product, the dataset being represented as:

$$D=\{(X_1,y_1),(X_2,y_2),\ldots,(X_n,y_n)\}$$

where n is a total number of the samples, p is a total number of the gene-related biological features such that $X_i=(x_{i1}, x_{i2}, \ldots, x_{ip})$ is the $i^{th}$ sample with p gene-related biological features and $y_i$ is a corresponding dependent variable; and processing, using one or more processors, the biological data using the solved regression model so as to determine, from the plurality of gene-related biological features, one or more of the gene-related biological features that are associated with cancer, wherein the regression model involves a linear combination of $L_{1/2}$-regularized logistic regression and $L_2$-regularized logistic regression, and is defined by:

$$L(\lambda, \alpha, \beta) = -\sum_{i=1}^{n}\{y_i \log[f(X_i'\beta)] + (1-y_i)\log[1-f(X_i'\beta)]\} + \lambda\left(\alpha|\beta|^{\frac{1}{2}} + (1-\alpha)|\beta|^2\right)$$

where L is a function of the regression model, $X'_i$ is a transpose of $X_i$, $$f(X_i'\beta) = \frac{e^{(X_i'\beta)}}{1+e^{(X_i'\beta)}},$$

$\beta=(\beta_1, \ldots, \beta_p)$, $\beta_1$ to $\beta_p$ are the parameters to be determined or optimized, and $\lambda$ and $\alpha$ are regularization parameters having predetermined values.

2. The method in accordance with claim 1, wherein $\lambda=1$ and $\alpha=0.2$.

3. The method in accordance with claim 1, wherein the parameters in the regression model are determined or optimized, using the one or more processors, based on a coordinate descent optimization method.

4. The method in accordance with claim 3, wherein the coordinate descent optimization method comprises the steps of:
   optimizing the regression model using at least some of the biological data, by varying one of the parameters in the regression model while fixing other of the parameters in the regression model; and
   updating the parameters in the regression model;
   wherein the optimizing and updating steps are performed at least once for each of the parameters in the regression model so as to optimize the regression model.

5. The method in accordance with claim 4, wherein the coordinate descent optimization method continues until a convergence condition relating to the parameters in the regression model is reached.

6. The method in accordance with claim 1, further comprising the step of:
   ranking, using the one or more processors, the gene-related biological features determined to be associated with the medical condition according to their degree of association with the cancer.

7. The method of claim 1, further comprising: displaying, at a display operably connected with the one or more processors, the determination result.

8. A system for determining association of gene-related biological features with a cancer, comprising:
   one or more processors arranged to:
   process at least some of biological data in a dataset using a regression model to determine or optimize parameters in the regression model thereby solving the regression model, the biological data being related to a plurality of samples taken from humans at least some of which have the cancer, each of the plurality of samples including a plurality of gene-related biological features of the following type: presence of a gene, gene expression, presence of a gene product, or amount of a gene product, the dataset being represented as:

$$D=\{(X_1,y_1),(X_2,y_2),\ldots,(X_n,y_n)\}$$

where n is a total number of the samples, p is a total number of the gene-related biological features such that $X_i=(x_{i1}, x_{i2}, \ldots, x_{ip})$ is the $i^{th}$ sample with p gene-related biological features and $y_i$ is a corresponding dependent variable; and process the biological data using the solved regression model so as to determine, from the plurality of gene-related biological features, one or more of the gene-related biological features that are associated with cancer, wherein the regression model involves a linear combination of $L_{1/2}$-regularized logistic regression and $L_2$-regularized logistic regression, and is defined by:

$$L(\lambda, \alpha, \beta) = -\sum_{i=1}^{n}\{y_i \log[f(X_i'\beta)] + (1-y_i)\log[1-f(X_i'\beta)]\} + \lambda\left(\alpha|\beta|^{\frac{1}{2}} + (1-\alpha)|\beta|^2\right)$$

where L is a function of the regression model, $X'_i$ is a transpose of $X_i$, $$f(X_i'\beta) = \frac{e^{(X_i'\beta)}}{1+e^{(X_i'\beta)}},$$

$\beta=(\beta_1, \ldots, \beta_p)$, $\beta_1$ to $\beta_p$ are the parameters to be determined or optimized, and $\lambda$ and $\alpha$ are regularization parameters having predetermined values.

9. The system in accordance with claim 8, wherein $\lambda=1$ and $\alpha=0.2$.

10. The system in accordance with claim 8, wherein the one or more processors are further arranged to determine or optimize the parameters in the regression model by
   optimizing the regression model using at least some of the data, through varying one of the parameters in the regression model while fixing other of the parameters in the regression model; and
   updating the parameters in the regression model;
   wherein the optimizing and updating are performed at least once for each of the parameters in the regression model until a convergence condition relating to the parameters in the regression model is reached.

11. The system in accordance with claim 8, wherein the one or more processors are further arranged to rank the gene-related biological features determined to be associated with the cancer according to their degree of association with the cancer.

12. The system in accordance with claim 8, further comprising a display operably connected with the one or more processors to display the determination result.

13. A non-transient computer readable medium for storing computer instructions that, when executed by one or more processors, causes the one or more processors to perform a method for determining an association of one or more gene-related biological features with a cancer, comprising the steps of:
   processing at least some of biological data in a dataset using a regression model to determine or optimize parameters in the regression model thereby solving the regression model, the biological data being related to a plurality of samples taken from humans at least some of which have the cancer, each of the plurality of samples including a plurality of gene-related biological features of the following type: presence of a gene, gene expression, presence of a gene product, or amount of a gene product, the dataset being represented as:

$$D=\{(X_1,y_1),(X_2,y_2),\ldots,(X_n,y_n)\}$$

where n is a total number of the samples, p is a total number of the gene-related biological features such that $X_i=(x_{i1},$ $x_{i2}, \ldots, x_{ip}$) is the $i^{th}$ sample with p gene-related biological features and $y_i$ is a corresponding dependent variable; and processing the biological data using the solved regression model so as to determine, from the plurality of gene-related biological features, one or more of the gene-related biological features that are associated with cancer, wherein the regression model involves a linear combination of $L_{1/2}$-regularized logistic regression and $L_2$-regularized logistic regression, and is defined by:

$$L(\lambda, \alpha, \beta) = -\sum_{i=1}^{n} \{y_i \log[f(X_i'\beta)] + (1-y_i)\log[1-f(X_i'\beta)]\} + \lambda\left(\alpha|\beta|^{\frac{1}{2}} + (1-\alpha)|\beta|^2\right)$$

where L is a function of the regression model, $X'_i$ is a transpose of $X_i$, $$f(X_i'\beta) = \frac{e^{(X_i'\beta)}}{1+e^{(X_i'\beta)}},$$

$\beta = (\beta_1, \ldots, \beta_p)$, $\beta_1$ to $\beta_p$ are the parameters to be determined or optimized, and $\lambda$ and $\alpha$ are regularization parameters having predetermined values.

* * * * *